United States Patent [19]

Gero et al.

[11] 4,377,704

[45] Mar. 22, 1983

[54] HETERO-PROSTAGLANDIN DERIVATIVES AND PROCESSES FOR PREPARING THEM

[75] Inventors: Stephan Gero, Les Ulis; Jeanine Cleophax, Palaiseau; Jean-Claude Barriere, Massy; Andre Cier, Neuilly-sur-Seine, all of France

[73] Assignee: Sanofi, Paris, France

[21] Appl. No.: 289,391

[22] Filed: Aug. 3, 1981

[51] Int. Cl.³ ............... C07C 47/40; C07D 319/06; C07D 339/06; C07D 407/08

[52] U.S. Cl. .................. 549/39; 549/374; 549/375; 568/446; 560/121; 562/503; 424/305; 424/317

[58] Field of Search ............ 260/340.9 P; 549/39; 568/442, 330, 379, 440; 544/374, 375

[56] References Cited

U.S. PATENT DOCUMENTS 3,664,502  2/1972  Morin et al. ............ 562/503
4,229,592 10/1980  Mitscher et al. .......... 560/231

OTHER PUBLICATIONS

McComie, Protective Groups in Organic Chemistry, p. 95, (1973).

Gill et al., Tetrahedron Letters, 22, 1437, (1981).

*Primary Examiner*—Robert Gerstl
*Attorney, Agent, or Firm*—Mason, Kolehmainen, Rathburn & Wyss

[57] ABSTRACT

Prostanoic acid derivatives represented by the general formula:

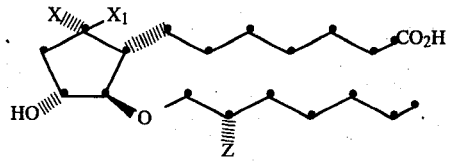

in which X represents hydrogen or hydroxy, $X_1$ represents hydrogen or X and $X_1$, when they are taken together with the carbon atom to which they are attached, represent a carbonyl group and Z represents hydrogen or hydroxy and pharmaceutically acceptable alkali metal salts thereof.

They can be used as bronchodilators and/or inhibitors of blood-platelet aggregation.

8 Claims, No Drawings

HETERO-PROSTAGLANDIN DERIVATIVES AND PROCESSES FOR PREPARING THEM

This invention relates to prostaglandin derivatives and is concerned with novel compounds related in structure to prostanoic acid which has the structural formula:

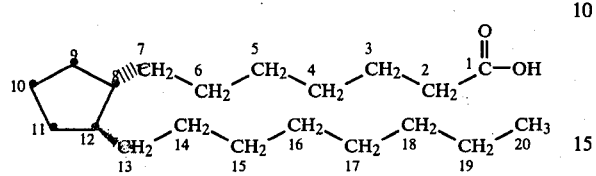

and which, in accordance with common usage, can also be written as follows:

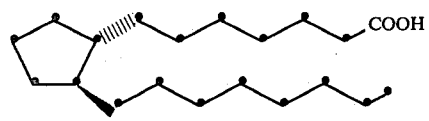

The present invention is also concerned with a process for preparing the said novel compounds.

The prostaglandin derivatives of the invention which are 13-oxa-prostaglandins, can be represented by the general formula:

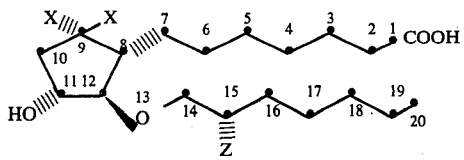

in which X represents hydrogen or hydroxy, $X_1$ represents hydrogen or X and $X_1$ when they are taken together with the carbon atom to which they are attached represent a carbonyl group and Z represents hydrogen or hydroxy.

The invention also relates to the pharmacologically acceptable salts of the compounds of formula I such as, for example, the salts resulting from the action of the said compounds of formula I and an alkali metal hydroxide such as sodium hydroxide.

Another object of the invention is to provide novel chiral compounds. These compounds are particularly useful as intermediate compounds for preparing prostaglandin derivatives and especially the prostaglandin derivatives of formula I above.

The novel chiral compounds in question are cyclopentene derivatives which can be represented by the general formula:

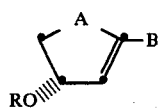

in which R represents a hydroxy-protecting group of the formula —$CH_2R_1$ in which $R_1$ represents an aryl or aralkyl radical, B represents

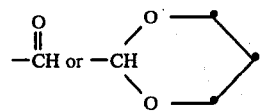

and A is such that: when B represents

A represents

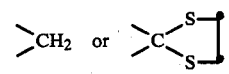

when B represents

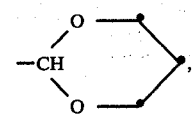

A represents

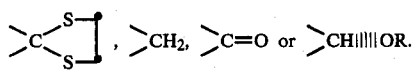

With respect to $R_1$, suitable meanings for aryl can be, for instance, phenyl substituted or not by a methyl radical and for aralkyl appropriate values can be, for example, benzyl substituted or not in the aromatic moiety by a methyl radical.

As a preferred value for R, benzyl can be cited. Thus, preferred compounds covered by general formula Ia, are the following:

2-Formyl-4 (R)-benzyloxy-2-cyclopentenone-ethylenedithioacetal referred to hereinafter as "Synthon A".

2-Formylpropyleneacetal-4 (R)-benzyloxy-2-cyclopentenone-ethylenedithioacetal referred to hereinafter as "Synthon B".

2-Formylpropyleneacetal-4 (R)-benzyloxy-2-cyclopentenone referred to hereinafter as "Synthon C".

2-Formylpropyleneacetal-4 (R)-benzyloxy-2-cyclopentenol referred to hereinafter as "Synthon D".

1-Formyl-3 (R)-benzyloxy-1-cyclopentene referred to hereinafter as "Synthon E".

1-Formylpropyleneacetal-3 (R)-benzyloxy-1-cyclopentene referred to hereinafter as "Synthon F".

Yet another object of the invention is concerned with a process for preparing the compounds of formula Ia.

The invention is also concerned with a method of using Synthons A to F as intermediate products for the preparation of the compounds of formula I above.

For the last fifteen years or so, prostaglandins have constituted a diversified and actively investigated research field. The chemical work that has been done in this field has resulted in the total synthesis of numerous prostaglandins and their analogs.

Since thromboxan ($TXA_2$) and prostacyclin ($PGI_2$) were discovered with their physiological activities which oppose each other, a considerable amount of research work has been devoted to this type of compound. Both substances are biosynthetized in living organisms from arachidonic acid via endoperoxide (PGH$_2$). Thromboxans are formed in human platelets and induce platelet aggregation, whereas prostacyclin, which is released from the vascular walls, inhibits such aggregation. Thus, theoretically, these two compounds regulate the formation of each other and failure or disturbance of this process of regulation causes the TXA$_2$-PGI$_2$ balance to be upset which in turn leads to cardiovascular diseases such as thrombosis, infarction and the like.

Prostanoic acid derivatives having a 13-heteroatom and endowed with an inhibitory action on platelet aggragation have already been described in British Patent Application No. 2,028,805 A and in J. Med. Chem. vol. 22, No. 11 pp. 1402-1408 (1979).

In British Patent Application No. 2,028,805 A the heteroatom is nitrogen while in the J. Med. Chem. reference in question the heteroatom is oxygen, a two-nitrogen bridge being fixed between the 9- and 11-positions giving rise to a 9,11-azo derivative.

It has now been found that a new series of prostanoic acid derivatives, namely 11-hydroxy-prostanoic acid derivatives, in which the carbon atom in the 13-position has been replaced by an oxygen atom, presents pharmacological properties generally found in the prostaglandin series, more particularly an inhibitory effect on blood-platelet aggregation and/or a bronchodilating action.

In view of their pharmacological properties, the 13-oxa-prostaglandin derivatives of the invention are capable of being used therapeutically in the treatment of pathological states which affect the respiratory system, and especially asthma. Furthermore, these compounds can be used as antithrombotic agents and in the treatment and prevention of cardiovascular diseases or pathological conditions such as myocardial infarction.

Therefore, another object of the invention relates to a method of provoking bronchodilation or inducing inhibition of blood-platelet aggregation in a host needing such treatment, method which comprises administering to said host an effective amount of at least one 13-oxa-prostaglandin of the invention.

For human therapy the compounds of the invention will be used at daily dosages of 0.1 to 40 mg/kg by oral route and of 0.3 to 120 mg by aerosol administration.

Yet another object of the present invention is to provide pharmaceutical and veterinary compositions comprising as an essential active ingredient at least one oxa-prostaglandin of formula I or a pharmaceutically acceptable salt thereof, in association with a pharmaceutical carrier or excipient therefor.

All the compounds of the invention can be obtained from Synthons A to F. The process for preparing these Synthons A to F comprises a number of original steps starting from (3R, 4S, 5R)-3,4-O-cyclohexylidene-3,4,5-trihydroxy-cyclohexanone, this latter compound being obtained from quinic acid, as described, for instance, by CLEOPHAX, LEBOUL, GERO, AKHTAR, BARNETT, PEARCE in J.A.C.S., 1976, 98, 7110.

The process of the invention for the preparation of the chiral intermediate compounds in question as well as for the preparation of the 13-oxa-prostaglandins of the invention can be summarized as follows:

A. Preparation of Synthon A (a) Reaction of (3R, 4S, 5R)-3,4-O-cyclohexylidene-3,4,5-trihydroxy-cyclohexanone of formula:

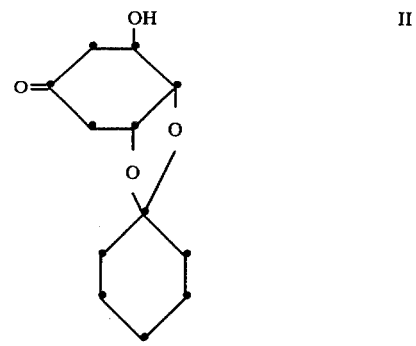

in the presence of boron trifluoride etherate, with ethanedithiol at room-temperature and in an aprotic solvent such as, for example, benzene, toluene, chloroform or dichloromethane, to provide (3R, 4S, 5R)-3,4,5-trihydroxy-cyclohexanone-ethylenedithioacetal of formula:

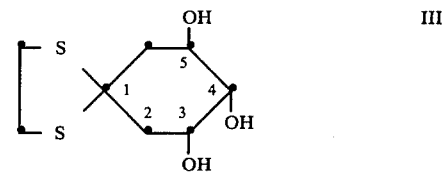

(b) Treatment of the dithioacetal III with 1,1-dimethoxycyclohexane in the presence of an acid catalyst such as, for example, sulphuric acid or p-toluenesulphonic acid, at room-temperature and in an aprotic solvent, for instance, N,N-dimethylformamide, to obtain (3R, 4S, 5R)-3,4-O-cyclohexylidene-3,4,5-trihydroxy-cyclohexanone-ethylenedithioacetal of formula:

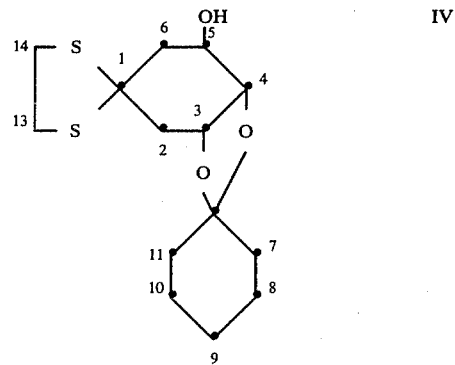

(c) Protection of the free hydroxyl group of compound IV with a bromide of the formula R Br in which R has the same meaning as above, preferably benzyl, in the presence of an alkali metal hydride, for instance sodium hydride, preferably at 0° C. and in an aprotic solvent such as, for instance, N,N-dimethylformamide, dimethylsulfoxide or hexamethylenephosphoramide to provide (3R, 4S, 5R)-3,4-O-cyclohexylidene-3,4,5-trihydroxycyclohexanone-ethylenedithioacetal derivatives of general formula:

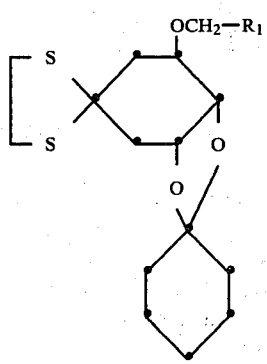

in which $R_1$ has the same meaning as above and which can be used either isolated or not in the following step:

(d) Treatment of the ether V with a strong inorganic acid, for instance hydrochloric acid, in an alcohol, for instance methanol, ethanol or isopropanol, and at the reflux temperature of the medium, to provide (3R, 4S, 5R)-3,4,5-trihydroxy-cyclohexanone-ethylenedithioacetal derivatives of general formula:

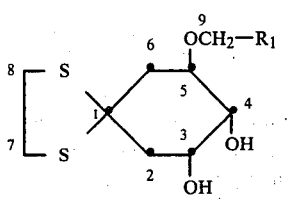

in which $R_1$ has the same meaning as above.

(e) Oxidation of the diol VI by means of neutral lead tetraacetate or triphenylbismuth carbonate in an appropriate solvent, for example, toluene, and at room-temperature, to obtain 4-oxo-ethylenedithioacetal-hexanedial derivatives of general formula:

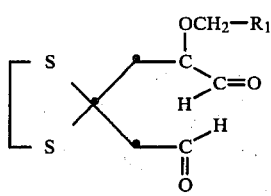

in which $R_1$ has the same meaning as above.

(f) Cyclisation of the acyclic dialdehyde VII in situ and under inert atmosphere with pyrrolidine acetate or piperidine acetate in an appropriate solvent, such as benzene or toluene, and at a temperature ranging from $-10°$ C. to room-temperature, preferably at $0°$ C., to obtain 2-formyl-2-cyclopentenone-ethylenedithioacetal derivatives of general formula:

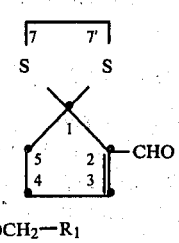

in which $R_1$ has the same meaning as given above or Synthon A.

B. Preparation of Synthon B

Synthon A hereabove is treated with 1,3-propanediol at room-temperature and in the presence of p-toluenesulfonic acid, the treatment being carried out in an anhydrous solvent, for example benzene or toluene, which provides 2-formylpropyleneacetal-2-cyclopentenone-ethylenedithioacetal derivatives of general formula:

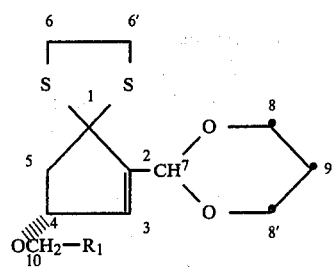

in which $R_1$ has the same meaning as given above for Synthon B.

C. Preparation of Synthon C

Synthon B is treated with neutral diphenylselenic anhydride at room-temperature and in an appropriate solvent, for instance dichloromethane, to provide 2-formylpropyleneacetal-2-cyclopentenone derivatives of general formula:

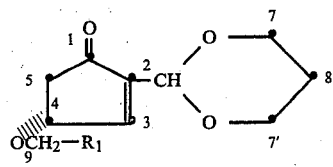

in which $R_1$ has the same meaning as given above or Synthon C.

D. Preparation of Synthon D

Synthon C is treated with diisobutyl aluminium hydride in an appropriate anhydrous solvent, for instance benzene or toluene, and at a temperature ranging from $-10°$ C. to room-temperature preferably at $0°$ C. to obtain 2-formylpropyleneacetal-2-cyclopentenol derivatives of general formula:

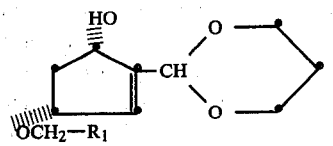

in which R₁ has the same meaning as given above or Synthon D.

E. Preparation of Synthon E (a) Treatment of diols VI above under reflux with Raney nickel (catalyst of finely divided nickel obtained by dissolving out with alkali the aluminium from a nickel-aluminium alloy) in an appropriate solvent, for instance ethanol, to provide (1R, 2S, 3R)-1,2,3-trihydroxy-cyclohexane derivatives of general formula:

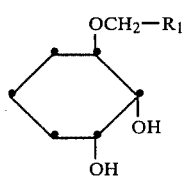   XII in which R₁ has the same meaning as given above.

(b) Oxidation of diols XII by means of neutral lead tetraacetate or triphenylbismuth carbonate in an appropriate anhydrous solvent, for example chloroform, and at room-temperature to obtain hexanedial derivatives of general formula:

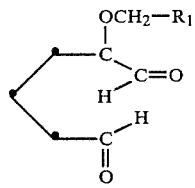   XIII in which R₁ has the same meaning as given above.

(c) Cyclisation of the acyclic dialdehydes XIII in situ and under inert atmosphere with pyrrolidine acetate or piperidine acetate in an appropriate solvent, such as toluene, and at a temperature ranging from −10° C. to room-temperature, preferably at 0° C., to obtain 1-formyl-1-cyclopentene derivatives of general formula:

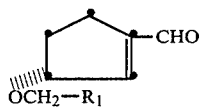   XIV in which R₁ has the same meaning as given above or Synthon E.

F. Preparation of Synthon F

Synthon E hereabove is treated with 1,3-propanediol at a temperature between room-temperature and 40° C., for instance at 30° C., and in the presence of p-toluenesulfonic acid, the treatment being carried out in an anhydrous solvent, for example benzene or toluene, which provides 1-formylpropyleneacetal-1-cyclopentene derivatives of general formula:

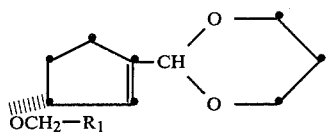   XV in which R₁ has the same meaning as given above or Synthon F.

G. Preparation of the 13-oxa-prostaglandins of formula I

Synthon B or Synthon F is first treated with boron hydride in tetrahydrofuran at a temperature ranging from 0° C. to room-temperature and the borane so formed is oxidized with hydrogen peroxide in the presence of sodium hydroxide, at a temperature ranging from 0° C. to room-temperature, to obtain cyclopentane derivatives of general formula:

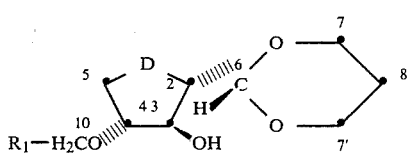   XVI in which D represents

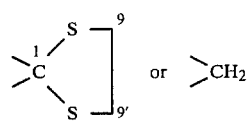

and R₁ has the same meaning as given above.

Different procedures are then applied to compounds XVI in accordance with the chemical structure of the 13-oxa-prostaglandin of formula I to be obtained.

I. When X and X₁ taken together with the carbon atom to which they are attached represent a carbonyl group and Z represents hydrogen or hydroxy.

(a) Treatment of compounds XVI in which D represents

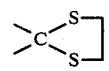

in the presence of an alkali metal hydride, for instance sodium hydride, at room-temperature and in an appropriate solvent, for example N,N-dimethylformamide, with a 1-halogeno-n-heptane derivative of general formula:

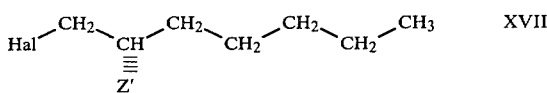   XVII in which Hal represents chlorine, bromine or iodine, and Z' represents hydrogen or a protected hydroxyl group of the formula OR in which R has the same value as given above, thus providing 2(S)-formylpropyleneacetal-3(R)-heptyloxy derivatives of general formula:

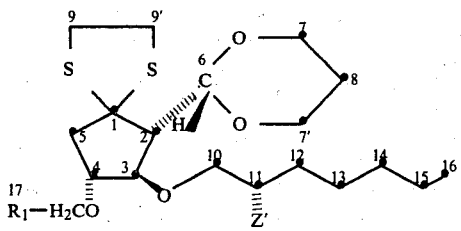
XVIII in which Z' and R₁ have the same meaning as given above.

(b) Hydrolysis of compounds XVIII in the presence of trifluoroacetic acid in chloroform or hydrochloric acid in acetone or hydrochloric acid in anhydrous chloroform/isopropanol, under inert atmosphere, to obtain 2(S)-formyl-3(R)-heptyloxy derivatives of general formula:

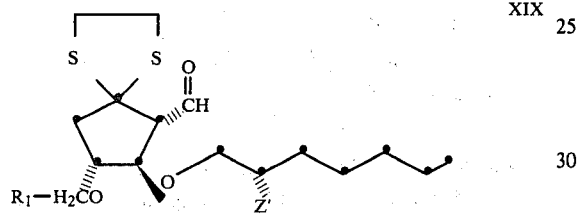
XIX in which Z' and R₁ have the same meaning as given above.

(c) Treatment of compounds XIX under inert atmosphere, with the dianion of (5-carboxypentyl)-triphenylphosphonium bromide at room-temperature and in an appropriate anhydrous solvent such as, for instance, ethyl ether, in accordance with the conditions of the Wittig reaction, to obtain 2(S)-(6-carboxy-1-hexenyl)-3(R)-heptyloxy derivatives of general formula:

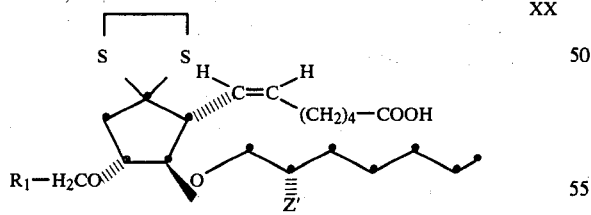
XX in which Z' and R₁ have the same meaning as given above.

(d) Deprotection of the hydroxyl groups of compounds XX by hydrogenolysis on platinum charcoal or palladium charcoal at room-temperature and in an appropriate medium, for instance an acetic acid/ethanol medium, to obtain 2(S)-(6-carboxyhexyl)-3(R)-heptyloxy derivatives of general formula:

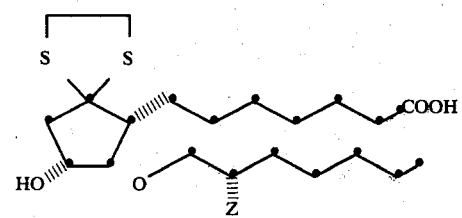
XXI in which Z has the same meaning as in formula I.

(e) Dethioacetalisation of compounds XXI with mercuric chloride in an appropriate solvent, such as acetone, and in the presence of boron trifluoride etherate to give 2(S)-(6-carboxyhexyl)-3(R)-heptyloxy derivatives of general formula:

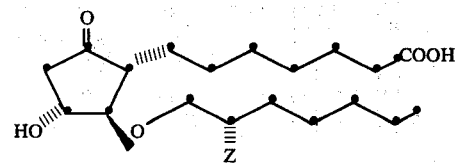

wherein Z has the same meaning as in formula I, which are the desired 13-oxa-prostaglandins of formula I.

II. When X and X₁ each are hydrogen and Z represents hydrogen or hydroxy (a) Treatment of compounds XVI with a n-halogenoheptane derivative as described in para G(Ia) hereabove to obtain:

when D represents >CH₂, 2(R)-heptyloxy-cyclopentane derivatives of general formula:

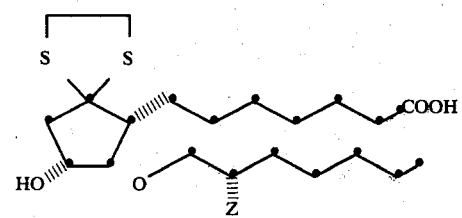
XXII in which Z' and R₁ have the same meaning as given above.

when D represents

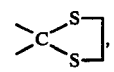

the compounds of formula XVIII above which, after reduction under reflux and on Raney nickel, provide a mixture of non-isolated products of general formula:

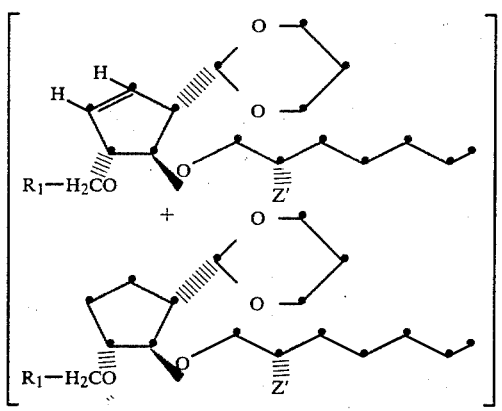

in which Z' and R₁ have the same meaning as given above, this mixture being further hydrogenated at atmospheric pressure on Adams platinum (catalyst of platinum oxide prepared from chloroplatinic acid) to give the compounds of formula XXII above.

(b) Hydrolysis of compounds XXII in the presence of an appropriate acid, for example trifluoroacetic acid or formic acid to give 2(R)-heptyloxy derivatives of general formula:

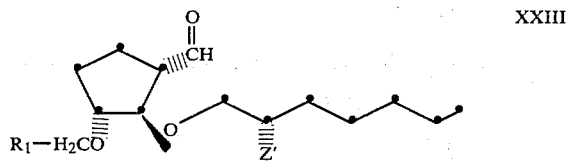  XXIII in which Z' and R₁ have the same meaning as given above.

(c) Treatment of compounds XXIII, under inert atmosphere, with the dianion of (5-carboxypentyl)-triphenylphosphonium bromide at room-temperature and in an appropriate anhydrous solvent, for instance ethyl ether or dimethylsulfoxide, in accordance with the conditions of the Wittig reaction to obtain 1(S)-(6-carboxy-1-hexenyl)-2(R)-heptyloxy derivatives of general formula:

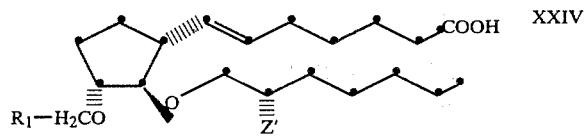  XXIV in which Z' and R₁ have the same meaning as given above.

(d) Deprotection of the hydroxyl groups of compounds XXIV by hydrogenolysis on platinum charcoal or palladium charcoal at room-temperature and in an appropriate medium, for instance an acetic acid/ethanol medium, to obtain 1(S)-(6-carboxyhexyl)-2(R)-heptyloxy derivatives of general formula:

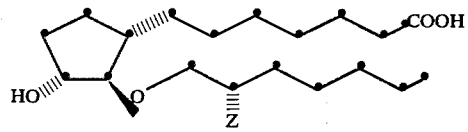

wherein Z has the same meaning as in formula I, which are the desired 13-oxa-prostaglandins of formula I.

III. When X represents hydroxy, X₁ represents hydrogen and Z represents hydrogen or hydroxy These compounds can be obtained starting from 2(S)-formylpropyleneacetal-3(R)-heptyloxy-cyclopentane derivatives of general formula:

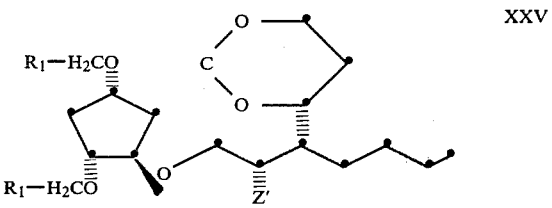  XXV in which Z' and R₁ have the same meaninbeing obtained in accordance with the following steps which comprise: either (a) Treatment of compounds XVI, in which D represents

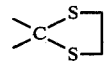

with a n-halogenoheptane as described in para G(Ia) hereabove to obtain compounds XVIII.

(b) Dethioacetalisation of compounds XVIII with mercuric chloride in an appropriate solvent, such as acetone, and in the presence of boron trifluoride etherate to give 1-oxo-3(R)-heptyloxy derivatives of general formula:

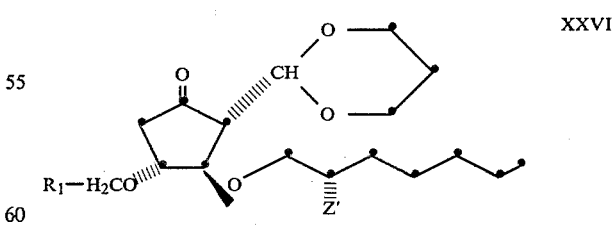  XXVI in which Z' and R₁ have the same meaning as given above.

(c) Reduction of the ketonic function using lithium tri-sec-butylborohydride as catalyst to give 3(R)-heptyloxy-cyclopentanol derivatives of general formula:

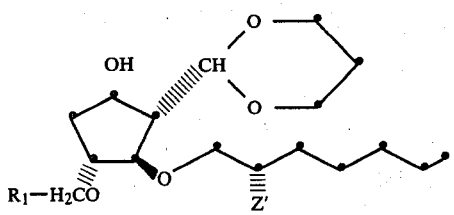

XXVII in which Z' and R₁ have the same meaning as given above.

(d) Protection of the free hydroxyl group of compounds XXVII with a bromide of the formula R Br in which R has the same meaning as above, preferably benzyl, in the presence of sodium hydride and in an appropriate aprotic solvent to give the 3(R)-heptyloxy-cyclopentane derivatives which correspond to the compounds of general formula XXV.

or (a) Protection of the free hydroxyl group of Synthon D with a bromide of the formula R Br in which R has the same meaning as above, preferably benzyl, in the presence of an alkali metal hydride, for instance sodium hydride, preferably at 0° C. and in an aprotic solvent such as, for instance, N,N-dimethylformamide, dimethylsulfoxide or hexamethylenephosphoramide, to provide 2-formylpropyleneacetal-2-cyclopentene derivatives of general formula:

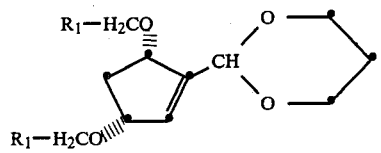

XXVIII in which R₁ has the same meaning as given above.

(b) Treatment of compounds XXVIII with boron hydride as described in para (G) hereabove to obtain 2(S)-formylpropyleneacetal-3(R)-hydroxy-cyclopentane derivatives of general formula:

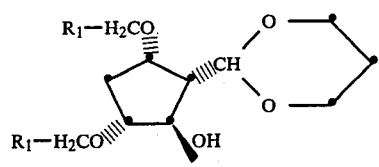

XXIX in which R₁ has the same meaning as given above.

(c) Treatment of compounds XXIX with a n-halogenoheptane derivative as described in para G(Ia) hereabove to obtain 2(S)-formylpropyleneacetalcyclopentane derivatives which correspond to the compounds of general formula XXV.

The compounds XXV above are then submitted to the following reactions.

(a) Hydrolysis in the presence of an appropriate acid, for example trifluoroacetic acid, to obtain 2(S)-formyl-cyclopentane derivatives of general formula:

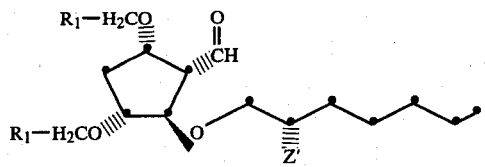

XXX in which Z' and R₁ have the same meaning as given above.

(b) Treatment of compounds XXX under inert atmosphere with the dianion of (5-carboxypentyl)-triphenylphosphonium bromide at room-temperature and in an appropriate anhydrous solvent such as, for instance, ethyl ether in accordance with the conditions of the Wittig reaction to obtain 2(S)-(6-carboxy-1-hexenyl)-cyclopentane derivatives of general formula:

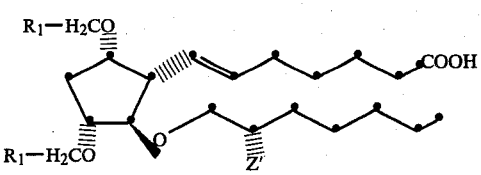

XXXI in which Z' and R₁ have the same meaning as given above.

(c) Deprotection of the hydroxyl groups of compounds XXXI by hydrogenolysis on platinum charcoal or palladium charcoal at room-temperature and in an appropriate medium, for instance an acetic acid/ethanol medium, to obtain 2(S)-(6-carboxyhexyl)-3(R)-heptyloxy derivatives of general formula:

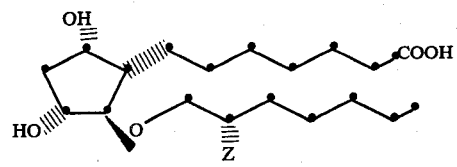

XXXII wherein Z represents hydrogen or hydroxy which are the desired 13-oxa-prostaglandins of formula I.

With respect to the pharmaceutically acceptable salts of the heteroprostaglandins of formula I, these will be obtained, in a classical manner, by reacting the acid of formula I with an appropriate alkali metal hydroxide, for instance, sodium hydroxide.

As regards the halogenoheptane derivatives of formula XVII in which Z' represents an —OR group, these can be obtained from (S)-(-)heptane-1,2-diol described by K. MORI in Agr. Biol. Chem. 40, 1617 (1976).

This diol is tritylated to obtain the 1-O-trityl derivative and the 2-hydroxy is then protected using a bromide of the formula R Br in which R has the meaning given above, preferably benzyl.

The 1-O-trityl is then deprotected and the free hydroxyl so regenerated is substituted by a halogen atom using conventional procedures so as to provide the compounds of formula XVII in which Z' represents the —OR group in question.

Tests were carried out in order to evaluate the pharmacological properties of the 13-oxa-prostaglandins of the invention.

Bronchodilatory action

This action was determined by verifying the relaxant action on the isolated guinea-pig trachea previously contracted with carbachol i.e. carbamoylcholin hydrochloride.

For this purpose, spiral strips of about 3 mm in width of the tracheal tissue were maintained in a survival medium. The isometric tension of the guinea-pig tracheal preparations was continuously registered. An initial tension of 8 g was applied to each preparation. After a rest period of 60 minutes, a submaximal contraction was obtained by adding carbachol to the bath. When the contractile response of the preparation became reproducible 11(R)-hydroxy-13-oxa-prostanoic acid of formula I was added to the bath either when the carbachol-induced contraction was at its maximum so as to appreciate its relaxant action or when the preparation was completely relaxed so as to evaluate the influence of the acid on the basal tonus.

Under these conditions, 11(R)-hydroxy-13-oxa-prostanoic acid provoked a moderate decrease of the basal tonus of the guinea-pig tracheal preparation.

The amplitude of this decrease depended on the dose employed of the prostanoic acid derivative.

Furthermore, the relaxant action at concentrations of about $10^{-5}$ and about $4.10^{-5}$ mol of 11(R)-hydroxy-13-oxa-prostanoic acid on preparations contracted by $8.10^{-8}$ mol of carbachol was also found to be moderate. In addition, it was found that the relaxant effect in question was not similar to a $\beta_2$-adrenoreceptor stimulant effect since in the presence of $10^{-5}$ mol of propranolol, the relaxant effect was not modified in either trial.

Inhibitory action on platelet aggregation

This test was performed in vitro on citrated human plasma using thrombine as aggregant agent.

Aggregation was carried out after incubation of the fraction of plasma rich in platelets for 20 min. at room-temperature in the presence of 5 µl of 11(R)-hydroxy-13-oxa-prostanoic acid of the invention in dimethylsulphoxide at a concentration of 1 mg/ml. The controls were incubated in a similar manner with 5 µl of dimethylsulphoxide.

The samples to be used for titration of thromboxane $B_2$ were taken after 3 min. aggregation using 0.4 U/ml of thrombine and in the presence of 100 µg/ml of indomethacine and 100 µg/ml of imidazole (100 µl per 400 µl of fraction rich in platelets).

The thromboxane $B_2$ was then determined.

In this test, the amounts of thromboxane $B_2$ found were 857 ng/ml when the studied compound was present.

This thus shows that when the oxa-prostaglandin of the invention was used there was a 77%-decrease in thromboxane $B_2$ and a 47%-inhibition of platelet aggregation.

The therapeutic compositions of the invention can be made up in any form which is suitable for their administration in human and veterinary therapy. For ease of administration, the composition will normally be made up in a dosage unit form appropriate to the desired mode of administration, for example, a compressed tablet for perlingual administration, a pill, a powder, a capsule, a syrup, an emulsion for oral administration, a suspension for oral or aerosol administration, a suppository for rectal administration or a sterile solution or suspension for parenteral administration.

The therapeutic compositions in question will be prepared in accordance with known techniques by associating at least one compound of the invention with an appropriate diluent or excipient and then, if required, making up the resulting admixture in the desired dosage unit form.

Examples of suitable diluents and excipients are distilled water, ethanol, talc, magnesium stearate, starches, sugars and cocoa butter.

The preparation of compounds of the invention is illustrate by the following Examples.

EXAMPLE 1

Preparation of 2-formyl-4(R)-benzyloxy-2-cyclopentenone-ethylenedithioacetal or Synthon A (compound VIII with $R_1$=phenyl)

(a) (3R, 4S, 5R)-3,4,5-trihydroxy-cyclohexanone-ethylenedithioacetal (compound III)

To 8 g of (3R, 4S, 5R)-3,4-O-cyclohexylidene-3,4,5-trihydroxy-cyclohexanone (compound II) dissolved in 40 ml of anhydrous chloroform, 16 ml of ethanedithiol and 1.6 ml of freshly distilled boron trifluoride etherate were added. After one hour at room-temperature, thin layer chromatography was performed (solvent: 3/1 chloroform/ethyl ether) and the starting compound was found to have disappeared. The desired compound III precipitated as it was formed in the reaction medium and was then dissolved by adding methanol. The solution was neutralized with sodium bicarbonate, filtered and the solvents were evaporated off. The resulting solid was dissolved again in hot acetone and the insoluble salts were then filtered.

In this manner, compound III was obtained after crystallization from acetone.

Yield: 95%.

M.P.: 129°–130° C.

$\alpha_D$: −41° (methanol, C=1.4% W/V).

(b) (3R, 4S, 5R)-3,4-O-cyclohexylidene-3,4,5-trihydroxy-cyclohexanone-ethylenedithioacetal (compound IV)

To 7 g of the previously obtained compound III, dissolved in 30 ml of N,N-dimethylformamide, were added 8 ml of 1,1-dimethoxycyclohexane and 0.5 ml of concentrated sulphuric acid. The methanol formed in the reaction was evaporated off from time to time using a water pump so as to facilitate a shift in equilibrium leading to the desired compound IV. The reaction was terminated after two days at room-temperature as determined by thin layer chromatography (solvent: 3/1 chloroform/ethyl ether). The solution was diluted with dichloromethane and neutralized with sodium bicarbonate. After filtration, the organic phase was washed with water and then dried on sodium sulphate and concentrated under reduced pressure.

In this manner, compound IV was obtained after crystallization from petroleum ether.

Yield: 95%.

M.P.: 138°–140° C.

$\alpha_D$: −44° (chloroform, C=1.02% W/V).

¹³C N.M.R.

| N° C.   | 1     | 2     | 3     | 4     | 5     | 6     | 7     | 8     |
|---------|-------|-------|-------|-------|-------|-------|-------|-------|
| δ (ppm) | 62.97 | 46.46 | 73.76 | 79.67 | 71.55 | 41.59 | 40.16 | 25.02 |
| N° C.   | 9     | 10    | 11    | 12    | 13    | 14    |       |       |
| δ (ppm) | 23.72 | 24.04 | 35.35 | 110.09| 38.01 | 38.21 |       |       |

(c) (3R, 4S, 5R)-3,4-O-cyclohexylidene-5-O-benzyl-3,4,5-trihydroxy-cyclohexanone-ethylenedithioacetal (compound V with $R_1$ = phenyl)

Into a three-necked flask were introduced 0.845 g of sodium hydride and 47 ml of N,N-dimethylformamide under nitrogen at 0° C. After that, 9 g of compound IV were added followed by 3.6 ml (1.3 equivalent) of benzyl bromide once the solid was dissolved. The reaction medium showed a orange-yellow colour. The reaction was terminated after three hours as determined by thin layer chromatography (solvent: 3/1 chloroform/ethyl ether). The hydride in excess was removed by adding methanol and the reaction mixture was first poured into iced water and then extracted with dichloromethane. The organic phase was washed with water and dried on sodium sulphate. Evaporation of the solvents gave a yellow oil.

In this manner, the required compound V was obtained after crystallization from aqueous ethanol.
Yield: 95%.
M.P.: 68°–69° C.
$\alpha_D$: −50° (chloroform, C=1.06% W/V).

| | Elemental analysis | | |
|---|---|---|---|
| $C_{21}H_{28}O_3S_2$ | | | Mol. Wt.: 392.587 |
| calculated (%) | C: 64.25 | H: 7.19 | S: 16.34 |
| found (%) | C: 64.15 | H: 6.96 | S: 16.52 |

(d) (3R, 4S, 5R)-5-O-benzyl-3,4,5-trihydroxy-cyclohexanone-ethylenedithioacetal (compound VI with $R_1$ = phenyl)

The following reaction was effected directly from the raw compound V (yellow oil) obtained previously.

In 120 ml of methanol were dissolved 12 g of raw compound V. After that, 10 ml of 12 N-hydrochloric acid were added and the medium was heated to 70° C.

When the hydrolysis was complete, as determined by thin layer chromatography (solvent: 3/1 chloroform/ethyl ether), the reaction medium was diluted with dichloromethane and neutralized with sodium bicarbonate. The solution was then filtered and evaporated. The residue was taken up in dichloromethane and the organic phase was washed with water, dried on sodium sulphate, filtered and evaporated.

In this manner, the required Compound VI was obtained after crystallization from ethanol or ethyl acetate.
Yield: 88%.
M.P.: 135°–136° C.
$\alpha_D$: −72° (chloroform, C=1.03% W/V).

| | Elemental analysis | | |
|---|---|---|---|
| $C_{15}H_{20}O_3S_2$ | | | Mol. Wt. 312.457 |
| calculated (%) | C: 57.66 | H: 6.45 | S: 20.53 |
| found (%) | C: 57.65 | H: 6.53 | S: 20.23 |

| | Elemental analysis | | |
|---|---|---|---|
| $C_{15}H_{20}O_3S_2$ | | | Mol. Wt. 312.457 |

¹³C N.M.R. ($d^5$ pyridine)

| N° C.   | 1    | 2    | 3    | 4    | 5    | 6    | 7    | 8    | 9    |
|---------|------|------|------|------|------|------|------|------|------|
| δ (ppm) | 65.4 | 40.2 | 69.2 | 72.3 | 79.3 | 46.4 | 38.2 | 39.5 | 71.4 |

(e) 2(R)-benzyloxy-4-oxoethylenedithioacetal-hexanedial (compound VII in which $R_1$ = phenyl)

In a coloured flask, 1.33 g (3 mM) of lead tetraacetate was dried using a vane pump so as to remove all traces of acetic acid. After this operation, 100 ml of anhydrous toluene and 0.624 g (2 mM) of compound VI previously obtained were added. The reaction medium was then stirred at room-temperature.

After an hour and a half, the reaction was terminated as determined by thin layer chromatography (solvent: 3/1 chloroform/ethyl ether) and 3 ml of ethylene glycol were then added to remove the lead tetraacetate in excess. When this excess has reacted, the solution became clear. The reaction medium was then diluted with dichloromethane and the organic phase was washed once with water, then with a saturated solution of sodium bicarbonate and finally with water to neutrality. The organic phase was then dried on sodium sulphate, filtered and evaporated.

In this manner, the required compound VII was obtained in a quantitative yield in the form of a colourless oil which acquired a yellow tint in the course of time and had therefore be used without delay.
$\alpha_D$: −11° (chloroform, C=2.4% W/V).

As this compound is a particularly unstable product, it was reduced for characterization purposes thus giving 2(R)-benzyloxy-4-oxoethylenedithioacetal-hexanediol.

| Elemental analysis of this diol | | | |
|---|---|---|---|
| $C_{15}H_{22}O_3S_2$ | | | Mol. Wt.: 314.473 |
| calculated (%) | C: 57.29 | H: 7.05 | S: 20.39 |
| found (%) | C: 57.03 | H: 6.47 | S: 20.18 |

$\alpha_D$: −20° (chloroform, C=1.4% W/V).

(f) 2-Formyl-4(R)-benzyloxy-2-cyclopentenone-ethylenedithioacetal (compound VIII in which $R_1$ = phenyl)

In 20 ml of anhydrous toluene, 0.620 g of the raw compound VII previously obtained was dissolved under nitrogen at 0° C. After that, 0.5 ml of a 1 N-solution of pyrrolidine acetate in anhydrous benzene was added. The reaction medium was allowed to stand for 18 hours at 0° C. under nitrogen. At the end of this reaction time, thin layer chromatography (solvent: 3/1 chloroform/ethyl ether) showed that the starting compound had completely disappeared. The reaction medium was then diluted with dichloromethane and the organic phase was washed with water to neutrality, dried on sodium sulphate, filtered and evaporated.

In this manner, the required compound VIII or Synthon A was obtained in the form of a pale yellow oil which was stored at 0° C. in a coloured flask.
Yield: 95%.

| N.M.R. of the proton at 60 MHz | |
|---|---|
| δ (ppm) | H |
| 2.7 | 2H$_5$ (A-B system octuplet) |
| 3.45 | 2H$_7$ + 2H$_{7'}$ (multiplet) |
| 4.4 | CH$_2$ (phenyl) (singlet) |
| 4.7 | H$_4$ (sextuplet) |
| 6.65 | H$_3$ (doublet) |
| 7.2 | phenyl |
| 9.5 | H$_6$ (singlet) |

I.R. (CHCl$_3$)
1685–1705 cm$^{-1}$ unsaturated α, β-aldehyde
M.S. (electron impact)
M$^{+\cdot}$ = 292 (201, 186, 91, 77, 65)

value had been eluted with ethyl acetate and the solvents had been filtered and evaporated off, a colourless oil was obtained.

In this manner, the required compound IX or Synthon B was obtained after crystallization from petroleum ether.

Yield: 80%.
M.P.: 70°–71° C.
α$_D$: +86° (chloroform, C=1.12% W/V).

EXAMPLE 3

Preparation of 2-formylpropyleneacetal-4(R)-benzyloxy-2-cyclopente-

| $^{13}$C N.M.R. (d$^5$ pyridine) | | | | | | | | | | | |
|---|---|---|---|---|---|---|---|---|---|---|---|
| N°C. | 1 | 2 | 3 | 4 | 5 | 6 | 6' | 7 | 8 | 8' | 9 | 10 |
| δ (ppm) | (*) | 146.3 | 131.6 | 80.3 | 53.8 | 41.3 | 40.5 | 97.3 | 67.3 | 67.3 | 25.8 | 70.9 |

(*) not identified on the spectrum (quaternary carbon)

Elemental analysis

C$_{18}$H$_{22}$O$_3$S$_2$    Mol. Wt.: 350.506
calculated (%)    C: 61.68    H: 6.32    S: 18.29
found (%)    C: 61.44    H: 6.28    S: 18.37

N.M.R. of the proton at 250 MHz (CHCl$_3$)

| δ (ppm) | H | |
|---|---|---|
| 7.34 | phenyl | |
| 6.34 | H$_3$ | J (H$_3$ − H$_4$) = 2Hz |
| 5.25 | H$_7$ | |
| 4.65 | H$_4$ | |
| 4.55 | CH$_2$ (phenyl) | |
| 4.22 | H$_{8a}$ + H$_{8'a}$ | |
| 3.9 | H$_{8e}$ + H$_{8'e}$ | |
| 3.4 | 2H$_6$ + 2H$_{6'}$ | |
| 2.95 | H$_{5b}$ | J(H$_{5b}$ − H$_{5a}$) = 13.5 Hz; J(H$_{5b}$ − H$_4$) = 6.5 Hz |
| 2.6 | H$_{5a}$ | J(H$_{5b}$ − H$_{5a}$) = 13.5 Hz; J(H$_{5a}$ − H$_4$) = 5 Hz |
| 2.2 | H$_{9a}$ | |
| 1.4 | H$_{9e}$ | |

EXAMPLE 2

Preparation of 2-formylpropyleneacetal-4(R)-benzyloxy-2-cyclopentenone-ethylenedithioacetal or Synthon B (compound IX in which R$_1$=phenyl)

The reaction was carried out directly from the previously obtained unsaturated α,β-aldehyde.

In 50 ml of dry toluene, 0.550 g of compound VIII obtained in Example 1 f was dissolved and 1.5 ml of 1,3-propanediol together with a trace of p-toluenesulphonic acid were then added. At the end of a 24-hour reaction time, ¾ of the volume was evaporated off using a rotatory evaporator. After that, 1.5 ml of 1,3-propanediol and 50 ml of anhydrous toluene were added to shift the equilibrium in favour of the desired compound. This operation was carried out again 24 hours later. The reaction was almost terminated after 72 hours as determined by thin layer chromatography (solvent: 3/7 ethyl acetate/petroleum ether). However, there was still some of the starting aldehyde (5 to 10%) left. The reaction medium was diluted with dichloromethane, and neutralized with sodium bicarbonate. After filtering the salts, the organic phase was washed with water, dried on sodium sulphate, filtered and evaporated. The compound so obtained was then separated by thin layer chromatography (solvent: 3/7 ethyl acetate/petroleum ether). After the strip with the lower Rf none or Synthon C (compound X in which R$_1$=phenyl)

To 0.180 g of compound IX obtained in Example 2 dissolved in 5 ml of anhydrous dichloromethane was added 0.203 g (1.1 equivalent) of diphenylselenic anhydride (Ph$_2$Se$_2$O$_3$) free from any trace of nitric acid.

After that, one drop of propylene oxide per 50 mg of starting compound was added so as to remove likely nitric acid remnants. At the end of a 20-hour reaction time, thin layer chromatography (solvent: 3/7 ethyl acetate/petroleum ether) showed that the starting compound had disappeared and that a compound with a lower Rf value had been formed.

The reaction medium was slightly diluted with dichloromethane, neutralized with sodium bicarbonate, filtered and separated by thin layer chromatography (solvent: 3/7 ethyl acetate/petroleum ether). The strip with the lower Rf value under U.V. light was eluted with ethyl acetate, filtered and the solvent was evaporated off.

In this manner, the required compound X or Synthon C was obtained in the form of a colourless oil cristallizing from petroleum ether.

Yield: 68%.
M.P.: 42°–43° C.
[α]$_D$ = +42° (chloroform, C=1 W/V).

Elemental analysis

-continued

| $C_{16}H_{18}O_4$ | Mol. Wt.: 274.316 | |
|---|---|---|
| Calculated (%) | C: 70.05 | H: 6.61 |
| found (%) | C: 70.14 | H: 6.60 |

N.M.R. of the proton at 250 MHz (CHCl$_3$)

| δ (ppm) | H |
|---|---|
| 7.7 | H$_3$ |
| 7.3 | phenyl |
| 5.3 | H$_6$ |
| 4.7 | H$_4$ |
| 4.6 | CH$_2$ (phenyl) |
| 4.18 | H$_{7a}$ + H$_{7'a}$ |
| 3.9 | H$_{7e}$ + H$_{7'e}$ |
| 2.75 | H$_{5b}$    $J(H_{5b} - H_{5a}) = 18.5$ Hz ; $J(H_{5b} - H_4) = 6$ Hz |
| 2.43 | H$_{5a}$    $J(H_{5b} - H_{5a}) = 18.5$ Hz ; $J(H_{5a} - H_4) = 2.5$ Hz |
| 2.15 | H$_{8a}$ |
| 1.35 | H$_{8e}$ |

EXAMPLE 4

Preparation of 2-formylpropyleneacetal-4(R)-benzyloxy-2-cyclopentenol or Synthon D (compound XI in which R$_1$=phenyl)

To 2.44 g of compound X obtained in Example 3 dissolved in 53 ml of anhydrous toluene, there were added, drop-by-drop, under nitrogen atmosphere and at 0° C., 13.1 ml of diisobutyl aluminium hydride (1 M commercial solution in hexane).

Thirty minutes later, thin layer chromatography (solvent: 3/1 chloroform/ethyl ether) showed that all the starting product has disappeared. The reaction was stopped by slowly adding methanol at 0° C. The solution was then poured into iced water saturated with sodium chloride and then taken up in dichloromethane. The organic fraction was dried on sodium sulphate and then evaporated to dryness. The oil so obtained was dissolved in a 3/1 mixture of chloroform/ethyl ether and this solution was first filtered on Celite (a commercially available diatomaceous silica product, the word "Celite" being a registered Trade Mark) and then evaporated to dryness. The desired product was crystallized from a dichloromethane/petroleum ether mixture. The mother-liquors showed in N.M.R. of the proton, the presence of another product which was the other isomer.

In this manner, the required compound XI or Synthon D was obtained.
Yield: 89%.
M.P.: 88°-90° C.

| Elemental analysis | | |
|---|---|---|
| $C_{16}H_{20}O_4$ | | Mol. Wt.: 276.336 |
| calculated (%) | C: 69.54 | H: 7.29 |
| found (%) | C: 69.36 | H: 7.30 |
| M.S. | | |
| M$^{+\cdot}$ = 276. | | |

EXAMPLE 5

Preparation of 1-formyl-3(R)-benzyloxy-1-cyclopentene or Synthon E (compound XIV in which R$_1$=phenyl)

(a) (1R, 2S, 3R)-3-O-benzyl-1,2,3-trihydroxy-cyclohexane (compound XII in which R$_1$=phenyl)

In 80 ml of 95°-ethanol was dissolved 1.3 g of compound VI obtained in Example 1d. When the product was completely dissolved, Raney nickel was added in considerable excess and the medium was refluxed for 12 hours. The reaction mixture was filtered on Celite and thoroughly rinsed with ethanol so as to eliminate all the Raney nickel. The oil so obtained was taken up in chloroform and filtered on Whatmann paper. The required compound crystallized from petroleum ether.

In this manner, the required compound XII was obtained in a yield of 70%.
M.P.: 59°-60° C. (petroleum ether).
α$_D$= −83° (chloroform, C=1.3 W/V).

| Elemental analysis | | |
|---|---|---|
| $C_{13}H_{18}O_3$ | | Mol. Wt.: 222.287 |
| calculated (%) | C: 70.24 | H: 8.16 |
| found (%) | C: 70.12 | H: 8.11 |
| M.S. | | |
| M$^{+\cdot}$ = 222 | | |

(b) 2(R)-benzyloxy-hexanedial (compound XIII in which R$_1$=phenyl)

In 120 ml of anhydrous chloroform was dissolved 2.34 g of compound XII previously obtained and 5.7 g of lead tetraacetate were added by small fractions. The reaction was carried out protected from light and followed by thin layer chromatography (solvent:ethyl acetate/petroleum ether). Ninety minutes later, the reaction terminated and ethyleneglycol was added to eliminate the lead tetraacetate in excess. When the solution was clear, it was taken up in dichloromethane washed with water, with sodium bicarbonate and again with water. The chloroform phase was dried on sodium sulphate and evaporated to dryness.

In this manner, the required compound XIII was obtained and directly reacted in the following step.
N.M.R. of the 2 aldehyde protons at 60 MHz: 9.6 ppm.
I.R. spectrum: CHO at 1720 cm$^{-1}$.

(c) 1-Formyl-3(R)-benzyloxy-1-cyclopentene (compound XIV in which R$_1$=phenyl

Compound XIII previously obtained was dissolved in 100 ml of dry toluene and reacted, under nitrogen atmosphere and at 0° C., with 1 ml of a 2 N benzene solution of pyrrolidine acetate. The reaction medium was allowed to stand for about 8 hours at 0° C. and then poured into iced water. After being taken up in dichloromethane, the organic phase was dried on sodium sulphate and concentrated under reduced pressure. The α,β-unsaturated aldehyde so obtained, in the form of a clear yellow oil, was relatively unstable and was directly used, without purification in the following step.

In this manner the required compound XIV or Synthon E was obtained.
N.M.R. at 60 MHz:

| δ (ppm) | H |
|---|---|
| 9.8 | aldehyde |
| 7.3 | phenyl |
| 6.8 | =CH |

I.R. spectrum: CHO α,β unsaturated: 1680 cm$^{-1}$ to 1710 cm$^{-1}$.

EXAMPLE 6

Preparation of 1-formylpropyleneacetal-3(R)-benzyloxy-1 cyclopentene or Synthon F (compound XV in which $R_1$=phenyl)

To compound XIII obtained in Example 5b dissolved in 100 ml of dry toluene, there were added 10 ml of 1,3-propanediol and a trace of p-toluenesulphonic acid. The mixture was stirred at 30° C. with a rotatory evaporator for one hour and then kept under stirring for a further 24 hours. When the reaction was terminated, the reaction medium was diluted with dichloromethane and neutralized with sodium bicarbonate.

After 30 minutes of stirring at room-temperature, the solution was filtered and extracted with dichloromethane. After being washed with water, the organic phase was dried on sodium sulphate and evaporated under reduced pressure to obtain a dark oil which was purified by thin layer chromatography (solvent ½ ethyl acetate/petroleum ether).

In this manner the required compound XV or Synthon F was obtained in the form of a colourless oil.

Yield: 55% (from compound XII).

$\alpha_D$= +74° (chloroform, C=1.4 W/V).

| Elemental analysis | | |
|---|---|---|
| $C_{16}H_{20}O_3$ | | Mol. Wt.: 260.333 |
| calculated (%) | C: 73.81 | H: 7.74 |
| found (%) | C: 73.81 | H: 7.71 |
| M.S. | | |
| $M^+$· = 260. | | |

EXAMPLE 7

Preparation of 11(R)-hydroxy-13-oxa-prostanoic acid ($X=X_1=Z=H$)

(a)

1(S)-formylpropyleneacetal-2(R)-hydroxy-3(R)-benzyloxy-cyclopentane (compound XVI in which D represents >CH$_2$ and $R_1$=phenyl)

In a three-necked flask maintained under nitrogen or argon atmosphere was dissolved 1.5 g of compound XV obtained in Example 6 or Synthon F in 20 ml of freshly distilled tetrahydrofuran. After cooling to 0° C., 2 equivalents of a 1 M commercial solution of boron hydride in tetrahydrofuran were added. The medium was allowed to stand at 0° C. and then for 15 minutes at room-temperature. After that, the reaction mixture was oxidized. For this purpose, the diborane in excess was destroyed at 0° C. by adding, drop-by-drop, 1 ml of water, then 1.5 ml of a 3 N-solution of sodium hydroxide and finally 3 ml of hydrogen peroxide. At the end of a 4-hour reaction-time, potassium carbonate was added. The mixture was diluted with ethyl ether and the ethereal phase was decanted out, washed with water, dried on sodium sulphate and evaporated under reduced pressure.

After separation by thin layer chromatography (solvent: ½ ethyl acetate/petroleum ether) there were obtained 0.950 g of the required alcohol (one isomer) and 0.190 g of the starting product.

In this manner, the required compound XVI was provided.

| Elemental analysis | | |
|---|---|---|
| $C_{16}H_{22}O_4$ | | Mol. Wt.: 278.348 |
| calculated (%) | C: 69.04 | H: 7.96 |
| found (%) | C: 68.85 | H: 7.94 |

$\alpha_D$= +5° (7.5 mg/ml).

(b)

1(S)-formylpropyleneacetal-2(R)-heptyloxy-3(R)-benzyloxy-cyclopentane (compound XXII in which Z'=H and $R_1$=phenyl)

Under nitrogen atmosphere and at 0° C., 0.390 g of the required compound XVI previously obtained was added in 10 ml of N,N-dimethylformamide, to 0.600 g of a oily suspension of sodium hydride. Once the hydrogen evolution terminated, 0.7 ml of n-iodoheptane was added and the temperature was allowed to return to room-temperature. Two hours later, the reaction was complete and the mixture was cooled to 0° C. and diluted with dichloromethane. The hydride in excess was destroyed by adding methanol and the solution was poured into iced water saturated with sodium chloride.

After extraction with dichloromethane, the organic phase was dried on sodium sulphate and then evaporated under reduced pressure. After separation by thin layer chromatography there was obtained 0.350 g of the required ether.

In this manner the required compound XXII was provided.

$\alpha_D$= +5° (chloroform, C=1 W/V).

| Elemental analysis | | |
|---|---|---|
| $C_{23}H_{36}O_4$ | | Mol. Wt.: 376.537 |
| calculated (%) | C: 73.26 | H: 9.63 |
| found (%) | C: 73.18 | H: 9.62 |

Using the same procedure, 1(S)-formylpropyleneacetal-2(R)-[2(S)-benzyloxyheptyloxy]-3(R)-benzyloxy-cyclopentane was prepared.

| Elemental analysis | | |
|---|---|---|
| $C_{29}H_{42}O_5$ | | Mol. Wt.: 470.650 |
| calculated (%) | C: 74.00 | H: 8.99 |
| found (%) | C: 73.96 | H: 8.95 |

(c)

1(S)-formyl-2(R)-heptyloxy-3(R)-benzyloxy-cyclopentane (compound XXIII in which Z'=H and $R_1$=phenyl)

Under nitrogen atmosphere, 0.740 g of the required compound XXII previously obtained was dissolved in 5 ml of anhydrous chloroform. After that, 20 ml of 80%-formic acid were added and the reaction was monitored by thin layer chromatography (solvent:chloroform). After 24 hours, a further quantity of 10 ml of formic acid was added and the reaction was allowed to stand under nitrogen atmosphere for 24 hours.

The reaction medium was cooled and sodium bicarbonate was added.

When the pH of the medium was 4, the solution was poured into iced water saturated with sodium chloride. The aqueous phase was taken up in dichloromethane. The organic phase was washed with an aqueous solution of sodium bicarbonate to neutrality and then with water. After drying on sodium sulphate and evaporation of the solvents in a coloured flask, 0.630 g of a clear yellow oil was obtained.

In this manner the required compound XXIII was provided.

I.R. spectrum:strip at 1705 cm$^{-1}$.

M.S.

M$^{+\bullet}$=318.

Using the same procedure, 1(S)-formyl-2(R)-[2(S)-benzyloxy-heptyloxy]-3(R)-benzyloxy-cyclopentane was prepared.

M.S.

M$^{+\bullet}$=424.

(d) 1(S)-(6-carboxy-1-hexenyl)-2(R)-heptyloxy-3(R)-benzyloxy-cyclopentane (compound XXIV in which Z'=H and R$_1$=phenyl)

To 0.940 g of sodium hydride were added 19.6 ml of freshly distilled dimethylsulphoxide and the mixture was heated to 70° C. for 1 hour. The solution of sodium methylsulphinyl methide, which became a greyish green colour, was then transferred to a three-necked flask containing 4.48 g of (5-carboxypentyl)-triphenylphosphonium bromide maintained under argon atmosphere. The medium, which immediately turned red, was allowed to stand for one hour at room-temperature.

After that, 0.624 g of compound XXIII previously obtained dissolved under argon atmosphere in 19 ml of dimethylsulphoxide was added drop-by-drop to the ylide solution. The reaction medium was then allowed to stand for about 8 hours at room-temperature. The mixture was then poured into iced water containing a little sodium bicarbonate and the flask was rinsed with a 1/1 mixture of ethyl ether/petroleum ether. The aqueous phase was collected and then acidified to pH=3 by adding oxalic acid. The aqueous phase was washed four times with ethyl ether and the ethereal phases were collected, dried on sodium sulphate and evaporated off under reduced pressure. The mixture so obtained was purified by chromatography on a column (eluent: 1/1 ethyl acetate/petroleum ether).

In this manner, the required compound XXIV was obtained.

Yield: 33%.

$\alpha_D$=−45° (chloroform, C=0.35 W/V).

| Elemental analysis | | |
|---|---|---|
| C$_{26}$H$_{40}$O$_4$ | | Mol. Wt.: 416.606 |
| calculated (%) | C: 74.95 | H: 9.68 |
| found (%) | C: 75.17 | H: 9.70 |
| M.S. | | |
| M$^{+\cdot}$ = 416 | | |

Using the same procedure, 1(S)-(6-carboxy-1-hexenyl)-2(R)-[2(S)-benzyloxyheptyloxy]-3(R)-benzyloxy-cyclopentane was prepared.

| Elemental analysis | | |
|---|---|---|
| C$_{32}$H$_{46}$O$_5$ | | Mol. Wt.: 510.715 |
| calculated (%) | C: 75.25 | H: 9.07 |
| found (%) | C: 75.19 | H: 9.0 |
| M.S. | | |
| M$^{+\cdot}$ = 510 | | |

(e) 11(R)-Hydroxy-13-oxa-prostanoic acid

Compound XXIV previously obtained was dissolved in a 1/1 mixture of acetic acid/ethanol in the presence of 10%-palladium charcoal. After a 48-hour period of hydrogenation in a Parr apparatus, the reaction medium was filtered on Whatmann paper and then chromatographed on a column.

In this manner 11(R)-hydroxy-13-oxa-prostanoic acid was obtained.

Yield: 90%.

$\alpha_D$=+19° (chloroform, C=0.73 W/V).

| Elemental analysis | | |
|---|---|---|
| C$_{19}$H$_{36}$O$_4$ | | Mol. Wt.: 328.497 |
| calculated (%) | C: 69.47 | H: 11.04 |
| found (%) | C: 69.54 | H: 10.97 |
| M.S. | | |
| M$^{+\cdot}$ = 328 | | |

Using the same procedure, 11(R)-hydroxy-13-oxa-15(S)-hydroxy-prostanoic acid was prepared.

| Elemental analysis | | |
|---|---|---|
| C$_{19}$H$_{36}$O$_5$ | | Mol. Wt.: 344.492 |
| calculated (%) | C: 66.24 | H: 10.53 |
| found (%) | C: 66.18 | H: 10.60 |
| M.S. | | |
| M$^{+\cdot}$ = 344 | | |

EXAMPLE 8

Preparation of 11(R)-hydroxy-13-oxa-prostanoic acid (a) 2(S)-formylpropyleneacetal-3(R)-hydroxy-4(R)-benzyloxy-cyclopentanoneethylenedithioacetal (compound XVI in which D represents

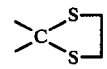

and R$_1$=phenyl)

In a 50 ml three-necked flask maintained under nitrogen atmosphere was dissolved 0.700 g of compound IX obtained in Example 2 or Synthon B in about 5 ml of freshly distilled tetrahydrofuran. Using a syringe, 10 ml of a 1 M-commercial solution of boron hydride (BH$_3$) in tetrahydrofuran was slowly added at 0° C. under nitrogen. The reaction medium was allowed to stand for about 15 hours at room-temperature during which time a light current of nitrogen was passed through the flask. The borane that formed was then oxidized. For this purpose the hydride in excess was removed by slowly adding water (about 2 ml) at 0° C. Still at the same temperature, 2 ml of a 3 N-solution of sodium hydroxide were added followed by 2 ml of 30%-hydrogen peroxide so as to oxidize the product. At the end of a 4-hour reaction-time, the reaction mixture was diluted with dichloromethane and poured into iced water saturated with ammonium chloride. The solution was taken up in dichloromethane and the organic phase was washed with water to neutrality, dried on sodium sulphate and evaporated off. The oil so obtained, which still contained some of the starting compound, was separated by thin layer chromatography and the product with the lower Rf value was collected (solvent: 1/1 ethyl ether/petroleum ether).

In this manner, the required compound XVI was obtained in the form of a colourless oil.

Yield: 35%.

$\alpha_D$: $-40°$ (CDCl$_3$, C=1.27% W/V).

Elemental analysis

| $C_{18}H_{24}S_2O_4$ | | Mol. Wt.: 368.52 |
|---|---|---|
| calculated (%) | C: 58.66 | H: 6.56 |
| found (%) | C: 58.99 | H: 6.74 |

N.M.R. of the proton at 250 MHz (CDCl$_3$/TMS)

| $\delta$ (ppm) | H |
|---|---|
| 1.4 | H$_{8e}$ |
| 2.1 | H$_{8a}$ |
| 2.37 | H$_{5a}$ + H$_2$ |
| 2.6 | H$_{5b}$ |
| 2.9 | OH (disappeared after addition of D$_2$O) |
| 3.21 | 2H$_9$ + 2H$_{9'}$ |
| 3.82 | H$_{7e}$ + H$_{7'e}$ |
| 3.95 | H$_3$ |
| 5 | H$_6$ |
| 5.18 | H$_{7a}$ + H$_{7'a}$ |
| 5.28 | H$_4$ |
| 5.6 | CH$_2$(10) |
| 7.35 | phenyl |

$^{13}$C N.M.R. (CDCl$_3$/TMS)

| N° C. | 1 | 2 | 3 | 4 | 5 | 6 |
|---|---|---|---|---|---|---|
| $\delta$ (ppm) | 66.3 | 60.6 | 79 | 82.6 | 49.5 | 103.8 |
| N° C. | 7 | 7' | 8 | 9 | 9' | 10 |
| $\delta$ (ppm) | 66.8 | 66.8 | 25.7 | 40.7 | 39.1 | 71.7 |

M.S.

M$^{+\cdot}$ = 368

(b)

2(S)-formylpropyleneacetal-3(R)-heptyloxy-4(R)-benzyloxy-cyclopentanoneethylenedithioacetal (compound XVIII in which Z′=H and R$_1$=phenyl)

Under nitrogen, a solution of 0.1 g of compound XVI previously obtained was added, in 5 ml of N,N-dimethylformamide, to a suspension of 0.04 g of sodium hydride in 5 ml of N,N-dimethylformamide.

Once hydrogen evolution was terminated, 0.7 g of n-iodoheptane was introduced. The reaction was monitored by thin layer chromatography (solvent: 1/1 ethyl ether/petroleum ether) and when this reaction terminated, the reaction medium was cooled to 0° C. and diluted with 10 ml of dichloromethane. The hydride in excess was removed by adding methanol. The solution was poured into sodium chloride-saturated iced water and then taken up in methylene chloride. The organic phase was washed three times with water, dried on sodium sulphate and concentrated. The resulting oil was then separated by thin layer chromatography (solvent: 1/1 ethyl ether/petroleum ether). In this manner, the required compound XVIII was obtained in the form of a colourless oil.

Yield: 60%.

Elemental analysis

| $C_{25}H_{38}O_4S_2$ | | Mol. Wt.: 466.71 | |
|---|---|---|---|
| calculated (%) | C: 64.34 | H: 8.20 | S: 13.74 |
| found (%) | C: 64.42 | H: 8.05 | S: 13.86 |

M.S.

M$^{+\cdot}$ = 466

13C N.M.R. (CDCl$_3$/TMS)

| N° C. | 1 | 2 | 3 | 4 | 5 | 6 | 7 | 7' |
|---|---|---|---|---|---|---|---|---|
| $\delta$ (ppm) | 67.8 | 58.6 | 84.5 | 84.1 | 48.2 | 102.7 | 66.3 | 66.5 |
| N° C. | 8 | 9 | 9' | 10 | 11 | 12 | 13 | 14 |
| $\delta$ (ppm) | 26 | 39 | 38.5 | 70.8 | 29.7 | 317 | 29 | 25.5 |
| N° C. | 15 | 16 | 17 | | | | | |
| $\delta$ (ppm) | 22.5 | 13 | 71.6 | | | | | |

N.M.R. of the proton at 250 MHz

| $\delta$ (ppm) | H |
|---|---|
| 0.9 | CH$_3$ (17) |
| 1.27 | CH$_2$ (13-14-15-16) |
| 1.55 | CH$_2$ (12) + H$_{8e}$ |
| 2.1 | H$_{8a}$ |
| 2.4 | H$_2$ + 2H$_5$ |
| 3.2 | 2(H$_9$ + H$_{9'}$) |
| 3.5 | CH$_2$ (11) |
| 3.8 | H$_{7e}$ + H$_{7'e}$ |
| 4.1 | H$_{7a}$ + H$_{7'a}$, H$_3$, H$_4$ |
| 4.6 | CH$_2$ (10) |
| 4.95 | H$_6$ (doublet) J(H$_6$ − H$_2$) = 10 Hz |
| 7.34 | phenyl |

(c)

1(S)-formylpropyleneacetal-2(R)-heptyloxy-3(R)-benzyloxy-cyclopentane (compound XXII in which Z′=H and R$_1$=phenyl)

A solution of 0.1 g of compound XVIII previously obtained in ethanol was refluxed for about 15 hours in the presence of Raney nickel. After filtration on Celite the mixture was evaporated to dryness.

The $^{13}$C N.M.R. and the proton N.M.R. spectra showed the presence of two products, one of which was unsaturated. The mixture was reduced, in the presence of Adams platinum and at atmospheric pressure, which led to one single compound.

In this manner, compound XVI was obtained.

Yield: 67%.

$\alpha_D$: $+5°$ (chloroform, C=10 mg/ml).

M.S.

M$^+$ = 376.

Elemental analysis

| $C_{23}H_{36}O_4$ | | Mol. Wt.: 376.537 |
|---|---|---|
| calculated (%) | C: 73.36 | H: 9.63 |
| found (%) | C: 73.18 | H: 9.62 |

$^{13}$C N.M.R. (CDCl$_3$/TMS)

| N° C. | 1 | 2 | 3 | 4 | 5 | 6 | 7 |
|---|---|---|---|---|---|---|---|
| $\delta$ (ppm) | 48.8 | 85.4 | 85 | 29.9 | 22.7 | 103.3 | 67 |
| N° C. | 7' | 8 | 9 | 10 | 11 | 12 | 13 |
| $\delta$ (ppm) | 67 | 25.8 | 69.7 | 29.9 | 31.8 | 29.2 | 26.1 |
| N° C. | 14 | 15 | 16 | | | | |
| $\delta$ (ppm) | 22.6 | 14.1 | 70.9 | | | | |

N.M.R. of the proton at 250 MHz

| $\delta$ (ppm) | H |
|---|---|
| 7.35 | phenyl |
| 4.55 | benzyl |
| 4.45 | H$_6$ (doublet) J (H$_6$ − H$_2$) = 6 Hz |
| 4.15 | H$_{7e}$ |

| | |
|---|---|
| 3.75 | H$_2$, H$_3$, H$_{7a}$ |
| 3.80 | multiplet O—CH$_2$ (9) (chain) |
| 2.05 | H$_1$ + H$_{8a}$ |
| 1.7 | 2H$_1$ + 2H$_5$ + H$_{8e}$ (complex mass) |
| 1.45 | CH$_2$ (10) |
| 1.3 | CH$_2$ (11-12-13-14) |
| 0.9 | CH$_3$ (15) |

(d)
1(S)-formyl-2(R)-heptyloxy-3(R)-benzyloxy-cyclopentane (compound XXIII in which R$_1$=phenyl)

In 4 ml of chloroform was dissolved 0.115 g of compound XXII previously obtained and then were added at 0° C. 3 ml of a 50%-aqueous solution of trifluoroacetic acid. The reaction medium was then allowed to stand for 36 hours at room-temperature. After dichloromethane had been added, the reaction medium was neutralized with sodium bicarbonate, filtered and taken up in water. The aqueous phase was washed with dichloromethane, dried and evaporated. The mixture residue so obtained contained 50% of the desired aldehyde and a residue of 40% constituted by the starting product. The aldehyde was separated by thin layer chromatography (solvent: chloroform). In this manner, compound XXIII was obtained.

M.S.

$M^{+\circ}=318$ (227, 155, 129, 107, 92, 91, 83, 67, 65, 57, 55).

N.M.R. of the proton at 60 MHz.

Doublet of the aldehyde proton at 9.2 ppm (e)
1(S)-(6-carboxy-1-hexenyl)-2(R)-heptyloxy-3(R)-benzyloxy-cyclopentane (compound XXIV in which Z'=H)

This compound was obtained in accordance with the method described in Example 7(d) above.

(f) 11(R)-Hydroxy-13-oxa-prostanoic acid

This compound was obtained in accordance with the method described in Example 7(e) above.

EXAMPLE 9

Preparation of 9(S)-hydroxy-11(R)-13-oxa-prostanoic acid (a)
1(S)-Benzyloxy-2-formylpropyleneacetal-4(R)-benzyloxy-2-cyclopentene (compound XXVIII in which R$_1$=phenyl)

To 0.187 g of sodium hydride were added 3 ml of N,N-dimethylformamide and the temperature was lowered to 0° C.

After that, 0.690 g of compound XI obtained in Example 4 or Synthon D, previously dissolved in 15 ml of N,N-dimethylformamide, were introduced followed by 0.637 g (1.5 equivalent) of benzyl bromide under nitrogen atmosphere and at 0° C. The medium was allowed to stand for 3 hours and monitored by thin layer chromatography (solvent 3/1 chloroform/ethyl ether). At the end of this period of time, the reaction medium was cooled and the hydride in excess was removed by adding methanol.

The solution was poured drop-by-drop into iced water and then taken up with dichloromethane. The organic phase was dried on sodium sulphate, filtered and evaporated to dryness.

In this manner, the required compound XXVIII was obtained in the form of a colourless oil.

Yield: 90%.

$a_D=+46°$ (chloroform, C=1.17 W/V).

| Elemental analysis | | |
|---|---|---|
| C$_{23}$H$_{26}$O$_4$ | | Mol. Wt.: 366.461 |
| calculated (%) | C: 75.38 | H: 7.15 |
| found (%) | C: 75.35 | H: 7.18 |
| M.S. | | |
| $(M^{+\cdot} - 1) = 365$ | | |

(b)
1(S)-Benzyloxy-2(S)-formylpropyleneacetal-3(R)-hydroxy-4(R)-benzyloxycyclopentane (compound XXIX in which R$_1$=phenyl)

The whole reaction was carried out under nitrogen atmosphere and the apparatus was previously dried at 150° C.

To 3.7 g of compound XXVIII previously obtained in 50 ml of freshly distilled tetrahydrofuran, was added drop-by-drop and at 0° C. 1 equivalent of a 1 M commercial solution of boron hydride in tetrahydrofuran. After that, the reaction medium was allowed to stand at 0° C. for 2 hours and then overnight at room-temperature. The hydride in excess was destroyed at 0° C. by slowly adding the minimum quantity of water. Oxidation to alcohol was obtained by adding, at 0° C., 2 ml of 6 N sodium hydroxide and 1.8 ml of 30%-hydrogen peroxide. The reaction was allowed to stand for 4 hours at room-temperature and then potassium carbonate was added. The mixture was filtered and copiously rinsed with ethyl ether.

The ethereal phase so obtained was dried on sodium sulphate, filtered and evaporated to dryness. The alcohol so provided was crystallized from aqueous ethanol and the resulting mother liquors were separated out by chromatography on a column of silica gel (solvent: ½ ethyl acetate/petroleum ether).

In this manner the required compound XXIX was obtained in a yield of 45%. M.P.: 76°–77° C. (ethanol/water)

$\alpha_D=+48°$ (chloroform, C=0.83 W/V).

| Elemental analysis | | |
|---|---|---|
| C$_{23}$H$_{28}$O$_5$ | | Mol. Wt.: 384.477 |
| calculated (%) | C: 71.85 | H: 7.34 |
| found (%) | C: 71.86 | H: 7.33 |

(c)
1(S)-Benzyloxy-2(S)-formylpropyleneacetal-3(R)-heptyloxy-4(R)-benzyloxycyclopentane (compound XXV in which Z'=H and R$_1$=phenyl)

In a three-necked flask were placed 3 equivalents of an oily suspension of sodium hydride under nitrogen atmosphere. After washing with dry hexane, 5 ml of N,N-dimethylformamide were added. The temperature was lowered to 0° C. and then 1 g of compound XXIX previously obtained dissolved in 15 ml of N,N-dimethylformamide, was added.

Once hydrogen evolution terminated, 1.4 ml of n-iodoheptane (Mol Wt. 229, d=1.37) was added. After about 8 hours at room-temperature, the reaction medium was cooled to 0° C., diluted with dichloromethane and the hydride in excess was removed by adding methanol. The solution was then poured into iced water saturated with sodium chloride taken up with dichloromethane and dried on sodium sulphate. After evaporation to dryness, the desired product so obtained was purified by chromatography on a silica gel column (solvent: ½ ethyl acetate/petroleum ether).

In this manner the required compound XXV was obtained in the form of a colourless oil.

Yield: 75%.

| Elemental analysis | | |
|---|---|---|
| $C_{30}H_{42}O_5$ | | Mol. Wt.: 482.66 |
| calculated (%) | C: 74.65 | H: 8.77 |
| found (%) | C: 74.59 | H: 8.82 |

$\alpha_D=0$ (chloroform, C=1.7 W/V).

Using the same procedure, 1(S)-benzyloxy-2(S)-formylpropyleneacetal-3(R)[2(S)-benzyloxy-heptyloxy]-4(R)-benzyloxy-cyclopentane was prepared.

| Elemental analysis | | |
|---|---|---|
| $C_{36}H_{48}O_6$ | | Mol. Wt.: 576.774 |
| calculated (%) | C: 74.96 | H: 8.38 |
| found (%) | C: 74.89 | H: 8.40 |

(d)
1(S)-Benzyloxy-2(S)-formyl-3(R)-heptyloxy-4(R)-benzyloxy-cyclopentane (compound XXX in which Z'=H and $R_1$=phenyl)

Under argon atmosphere, 1.5 ml of a 80%-aqueous solution of formic acid was added to 0.085 g (0.176 m mol) of compound XXV previously obtained. After about 8 hours at room-temperature, the reaction mixture was diluted with dry dichloromethane and sodium bicarbonate was added to obtain a pH of about 4. The solution was taken up with anhydrous chloroform, washed with water to neutral pH, dried on sodium sulphate, filtered and evaporated to dryness.

In this manner, 0.063 g of the required compound XXX was obtained in the form of an oil which eventually turned yellow.

Yield: 90%.
I.R. spectrum: CHO at 1720 cm$^{-1}$.

| Elemental analysis | | |
|---|---|---|
| $C_{27}H_{36}O_4$ | | Mol. Wt.: 424.581 |
| calculated (%) | C: 76.38 | H: 8.54 |
| found (%) | C: 75.98 | H: 8.49 |

Using the same procedure, 1(S)-benzyloxy-2(S)-formyl-3(R)-[2(S)-benzyloxy-heptyloxy]-4-(R)-benzyloxy-cyclopentane was obtained.

| Elemental analysis | | |
|---|---|---|
| $C_{34}H_{42}O_5$ | | Mol. Wt.: 530.705 |
| calculated (%) | C: 76.94 | H: 7.97 |
| found (%) | C: 77.0 | H: 8.01 |

(e)
1(S)-Benzyloxy-2(S)-(6-carboxy-1-hexenyl)-3(R)-heptyloxy-4(R)-benzyloxy-cyclopentane (compound XXXI in which Z'=H and $R_1$=phenyl)

This compound was obtained in accordance with the method described in Example 7(d) above.

| Elemental analysis | | |
|---|---|---|
| $C_{33}H_{46}O_5$ | | Mol. Wt.: 522.726 |
| calculated (%) | C: 75.82 | H: 8.87 |
| found (%) | C: 75.60 | H: 8.91 |

Using the same procedure, 1(S)-benzyloxy-2(S)-(6-carboxy-1-hexenyl)-3(R)-[2(S)-benzyloxy-heptyloxy]-4(R)-benzyloxy-cyclopentane was provided.

| Elemental analysis | | |
|---|---|---|
| $C_{40}H_{52}O_6$ | | Mol. Wt.: 628.85 |
| calculated (%) | C: 76.39 | H: 8.35 |
| found (%) | C: 76.10 | H: 8.39 |

(f) 9(S)-Hydroxy-11(R)-hydroxy-13-oxa-prostanoic acid

This compound was obtained in accordance with the method described in Example 7e above.

| Elemental analysis | | |
|---|---|---|
| $C_{19}H_{36}O_5$ | | Mol. Wt.: 344.492 |
| calculated (%) | C: 66.24 | H: 10.53 |
| found (%) | C: 65.95 | H: 10.80 |
| M.S. $M^{+\cdot}=344$ | | |

Using the same procedure, 9(S)-hydroxy-11(R)-hydroxy-13-oxa-15(S)-hydroxyprostanoic acid was obtained.

| Elemental analysis | | |
|---|---|---|
| $C_{19}H_{36}O_6$ | | Mol. Wt.: 360.491 |
| calculated (%) | C: 63.30 | H: 10.06 |
| found (%) | C: 63.33 | H: 9.85 |
| M.S. $M^{+\cdot}=360$ | | |

We claim:
1. A cyclopentene derivative represented by the formula:

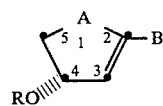

Ia in which R represents a hydroxy-protecting group of the formula —$CH_2R_1$ in which $R_1$ represents an phenyl or methylphenyl, B represents

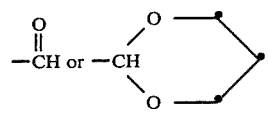

and A is such that: when B represents

A represents

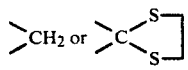

when B represents

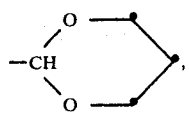

A represents

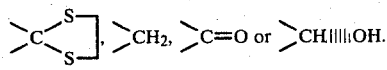

2. A cyclopentene derivative according to claim 1 wherein $R_1$ is phenyl.
3. 2-Formyl-4(R)-benzyloxy-2-cyclopentenoneethylenedithioacetal.
4. 2-Formylpropyleneacetal-4(R)-benzyloxy-2-cyclopentenone-ethylenedithioacetal.
5. 2-Formylpropyleneacetal-4(R)-benzyloxy-2-cyclopentenone.
6. 2-Formylpropyleneacetal-4(R)-benzyloxy-2-cyclopentenol.
7. 1-Formyl-3(R)-benzyloxy-1-cyclopentene.
8. 1-Formylpropyleneacetal-3(R)-benzyloxy-1-cyclopentene.

* * * * *

UNITED STATES PATENT AND TRADEMARK OFFICE
CERTIFICATE OF CORRECTION

PATENT NO. : 4,377,704
DATED : Mar. 22, 1983
INVENTOR(S) : Stephan Gero et al

It is certified that error appears in the above–identified patent and that said Letters Patent are hereby corrected as shown below:

Title page, first column, after item [22], insert the following:

[30] Foreign Application Priority Data

Aug. 12, 1980 [BR] United Kingdom 80 26240
May 1, 1981 [BR] United Kingdom 81 13487

Signed and Sealed this

Thirty-first Day of May 1983

[SEAL]

Attest:

DONALD J. QUIGG

Attesting Officer    Acting Commissioner of Patents and Trademarks